United States Patent [19]

Lauks et al.

[11] Patent Number: 5,609,824
[45] Date of Patent: Mar. 11, 1997

[54] METHODS AND APPARATUS FOR RAPID EQUILIBRATION OF DISSOLVED GAS COMPOSITION

[75] Inventors: Imants R. Lauks, Rockcliffe Park; Raymond J. Pierce, Ottawa, both of Canada; Joseph W. Rogers, Doylestown, Pa.; Michael P. Zelin, Brooklyn, N.Y.

[73] Assignee: i-Stat Corporation, Princeton, N.J.

[21] Appl. No.: 274,387

[22] Filed: Jul. 13, 1994

[51] Int. Cl.[6] .................................................. G01N 7/00
[52] U.S. Cl. .......................... 422/83; 204/403; 204/415; 204/431; 204/432; 205/782; 205/782.5; 422/68.1; 422/81; 422/82.02; 422/82.03; 422/82.04; 436/8; 436/9; 436/11; 436/16; 436/63; 436/67; 436/68; 436/138; 436/150; 436/151; 436/164; 436/168; 250/577; 73/1 G; 73/61.41
[58] Field of Search .................................. 204/403, 415, 204/431, 432, 153.17, 153.18, 153.16; 436/8, 9, 11, 16, 63, 68, 138, 150, 151, 168, 164; 422/68.1, 81, 83, 82.02, 82.03, 82.04; 250/577; 73/1 G, 61.41

[56] References Cited

U.S. PATENT DOCUMENTS

| | | | |
|---|---|---|---|
| 4,062,750 | 12/1977 | Butler et al. | 204/195 P |
| 4,116,336 | 9/1978 | Sorenson et al. | 206/524.8 |
| 4,426,451 | 1/1984 | Columbus | 436/518 |
| 4,534,356 | 8/1985 | Papadakis et al. | 128/635 |
| 4,635,467 | 1/1987 | Hoffa et al. | 73/1 G |
| 4,734,184 | 3/1988 | Burleigh et al. | 204/409 |
| 4,871,439 | 10/1989 | Enzer et al. | 204/401 |
| 5,046,496 | 9/1991 | Betts et al. | 128/635 |
| 5,096,669 | 3/1992 | Lauks et al. | 422/61 |
| 5,223,433 | 6/1993 | Deetz et al. | 436/8 |
| 5,231,030 | 7/1993 | Deetz et al. | 436/8 |
| 5,246,576 | 9/1993 | Leader et al. | 204/431 |
| 5,338,435 | 8/1994 | Betts et al. | 204/406 |
| 5,346,604 | 9/1994 | Van Sin et al. | 204/415 |
| 5,421,981 | 6/1995 | Leader | 204/409 |

OTHER PUBLICATIONS

Hahn, C.E.W., *J. Phys. E: Sci. Instrum.*, vol. 13, 1980.

Primary Examiner—Jill Warden
Assistant Examiner—Sharidan Carrillo
Attorney, Agent, or Firm—Lowe, Price, LeBlanc & Becker

[57] ABSTRACT

Disclosed is an apparatus and method of equilibrating the dissolved gas composition of an aqueous fluid to reflect the predetermined gas composition contained in a gas equilibration reservoir. The equilibrated aqueous fluid can be used in a method of determining the concentration of a dissolved gas in a fluid sample. In one embodiment, the disclosed method is used to control the equilibrated gas composition of a calibrant fluid which, in turn, is used to measure the concentration of a dissolved gas, such as oxygen and carbon dioxide, in a sample fluid, such as whole blood.

15 Claims, 4 Drawing Sheets

METHODS AND APPARATUS FOR RAPID EQUILIBRATION OF DISSOLVED GAS COMPOSITION

1. FIELD OF THE INVENTION

The present invention relates to methods of providing to a sensing device needing calibration, a calibrant fluid having a predetermined dissolved gas composition. In the present invention, the calibrant fluid having the predetermined dissolved gas composition is provided not by attempting to control the dissolved gas composition in the calibrant fluid while the calibrant fluid is in storage, but by rapidly equilibrating the dissolved gas composition of the calibrant fluid to the desired predetermined levels as the calibrant fluid is being brought into contact with the sensing device. This novel and remarkably efficient method is described in greater detail below. However, so that the reader may better appreciate the advance of the disclosed invention, the following discussion of the state of the art is provided without admitting that the same is available as prior art against the subject invention.

2. BACKGROUND OF THE INVENTION

2.1. General Calibration Methods for Blood Gas Analysis

Methods of calibrating an oxygen or carbon dioxide sensor for blood gas analyses are known which use wet gases of known composition. Concentrations of oxygen and carbon dioxide are selected to span the range of values anticipated for the clinical measurements. Typically, blood gas analyzers in current use require a two-point calibration method using wet gases of the following composition: 0% oxygen, 10% carbon dioxide, balance nitrogen; and, secondly, 12% oxygen, 5% carbon dioxide and balance nitrogen. Amperometric sensors such as those that measure oxygen concentration are calibrated at "zero" and at the high end of the range. The "zero" calibration is important as it enables any residual background current to be subtracted from the measurement. Potentiometric sensors, such as those for measuring carbon dioxide, are frequently calibrated at a "low" value and a "high" level. The gas mixtures used in the calibration are provided from cylinders equipped with pressure regulators which are attached directly to the analyzer. Such analyzers are commonly bench-top devices.

2.2. Specific Disclosures in the Field

More particularly, U.S. Pat. No. 5,231,030, issued to Deetz et al. Jul. 27, 1993, describes a temperature insensitive calibration system that consists of two phases: (i) an oxygen-containing perfluorocarbon solution; and (ii) a carbon dioxide-containing and solute-containing aqueous phase insoluble in the first phase. The solutes include carbon dioxide-complexing agents, ethylene diamine, bicarbonate, calcium ion, hydroxide ion and others. The multi-phase system is kept under a sealed storage atmosphere "which maintains the desired conditions in equilibrium during the shelf life of the system . . . ." The system disclosed is strictly for controlling the composition of the atmosphere during storage and does not contemplate control over the gas composition after a calibration fluid is released from the package used for storage.

A second Deetz et al. patent, U.S. Pat. No. 5,223,433, issued Jun. 29, 1993. Likewise, this patent discloses a system for controlling the concentration of gases in a sample "medium" independent of a given range of temperature. Control is said to be achieved by including a "reservoir" that is more responsive to changes in temperature than the sample "medium" itself. Thus, the atmosphere, which is common to both sample medium and reservoir, is replenished or depleted in gases almost exclusively from the contents of the reservoir which is made to respond to the changes effected by the change in temperature faster than the sample medium. In this way, the driving force for release or absorption of dissolved gases from the medium to the common atmosphere is adjusted as to diminish changes in the concentration of the dissolved gases in the medium in response to the changes in temperature. (See, in particular, the summary section of the specification.)

U.S. Pat. No. 5,096,669, granted to Lauks et al. Mar. 17, 1992 (the entire disclosure of which is incorporated herein by reference), discloses a disposable device similar to that described in the present invention, including housing, sensor, retaining means, and conduit. The '669 patent also discusses a pouch containing calibrant fluid for calibrating the sensors of the device. The subject matter of the present application is not disclosed, taught, or suggested however.

On the other hand, Enzer et al. in U.S. Pat. No. 4,871,439, which issued Oct. 3, 1989, disclose a disposable self-calibrating electrode package in which one or more containers of reference or calibrating electrolyte solution is present. Preferably, two containers having different compositions are used to allow the system to be calibrated on a two-point basis. (See, col. 4, line 26.) Oxygen and carbon dioxide electrode pairs are also described. U.S. Pat. No. 4,734,184, granted to Burleigh et al. Mar. 29, 1988, contains the same disclosure as the Enzer et al. '439 patent.

U.S. Pat. No. 4,116,336, granted to Sorensen et al. Sep. 26, 1978, describes a calibration packet containing a reference liquid "for the calibration and/or quality control of blood gas analyzers." The reference liquid is enclosed in a flexible, gas-tight container to the exclusion of any gas bubbles. (The total pressure in the liquid is kept below 600 mm Hg to avoid any danger of formation of gas bubbles.) Equilibration of the reference liquid gas composition over the sensor is not disclosed, taught or suggested. Moreover, this patent teaches that the transfer of the reference liquid from the package to the instrument should be done anaerobically. In addition, the '336 patent mentions equilibration only in the context of preparing a reference liquid prior to packaging. (Indeed, the equilibration process is performed overnight at a specified pressure of 600 mm Hg before packaging.)

U.S. Pat. No. 4,062,750 granted to Butler, Dec. 13, 1977, discloses a microfabrication method for the manufacture of thin film polarographic oxygen sensor. The gas permeable layer, which may be established by macro- or microfabrication methods, is, nevertheless intended to enclose both working and reference electrodes completely to form an enclosed structure. Further, at line 43 et seq. the '750 patent describes a recalibration method using room air and the sufficiency of a one point calibration. There is no discussion, however, regarding equilibration of a calibrant fluid.

Also, Hahn, C E W., in *J. Phys. E: Sci. Instrum.* (1980) 13:470–482, outlines a review article in which the principles of blood gas measurement are explored, with an extensive discussion of the historical development of blood gas analyzers. At section 3.2.4., calibration in both air and in liquids is described. Rapid control over the fluid gas composition in the proximity of the sensor itself is not a topic that is even broached. The disclosure also discusses electrodes for the measurement of partial pressure of carbon dioxide and nitrous oxide gases.

Thus, there remains a need for a calibration method that does not rely on control over the dissolved gas composition in a calibrant fluid in storage, which control can be difficult, and ultimately unreliable to maintain over a long period of storage.

3. SUMMARY OF THE INVENTION

The present invention relates to devices and methods of determining the dissolved gas composition of fluids, including biological fluid samples such as blood, plasma, and the like. It is thus an object of the present invention, to provide a cartridge for taking dissolved gas measurements in a fluid comprising: (a) a housing with a plurality of regions, including a sensor region and a calibrant fluid region; (b) a gas sensor located in the sensor region of the housing; (c) at least one conduit joining the sensor region with the calibrant fluid region of the housing; and (d) a gas equilibration reservoir containing a predetermined composition of calibrant gases, which reservoir is positioned in the conduit such that a calibrant fluid brought in contact with the reservoir undergoes a rapid exchange of the calibrant fluid's dissolved gases with those contained in the reservoir to provide a calibrant fluid with an equilibrated dissolved gas composition that reflects substantially the predetermined composition of calibrant gases contained in the reservoir. Moreover, the conduit and sensor region having a configuration which allows the displacement of the equilibrated calibrant fluid and a sample fluid across the gas sensor.

It is thus also an object of the present invention to provide a gas reservoir which can be charged with a predetermined composition of gases and which allows the rapid exchange of gases between the reservoir and an aqueous fluid with which it is in contact, such that the equilibrated dissolved gas composition in the aqueous fluid reflects substantially the predetermined composition of gases of the reservoir. Hence, according to the present invention, an apparatus is provided for the rapid equilibration of the dissolved gas composition of an aqueous fluid, which apparatus comprises: (a) a housing; (b) at least one conduit within the housing, which conduit can be charged with an aqueous fluid; and (c) a gas equilibration reservoir containing a predetermined composition of calibrant gases, which reservoir is positioned in the conduit such that an aqueous fluid brought in contact with the reservoir undergoes a rapid exchange of the aqueous fluid's dissolved gases with those contained in the reservoir to provide an aqueous fluid with an equilibrated dissolved gas composition that reflects substantially the predetermined composition of calibrant gases contained in the reservoir.

In one embodiment of the present invention, the housing is planar and may further comprise other conduits and regions, especially a second region within the housing for retaining a sample fluid, which second region is in fluid communication with the sensor. And in particular, the present invention contemplates a gas equilibration reservoir which includes a compartment filled with a solid or semi-solid material that functions as a source of or sink for a predetermined composition of calibrant gases. In select embodiments, the material comprises silicone rubber. In others, the material comprises a hydrogel. Still in others, the reservoir comprises a head space element or a plurality of head space elements. The reservoir and the conduit may optionally be separated by a gas permeable membrane.

It is also an object of the present invention to describe methods of determining the dissolved gas composition of a portion of a fluid comprising: (a) providing a conduit in fluid communication with a gas sensor, the conduit having a gas equilibration reservoir, e.g., a plurality of head space elements, which elements have a predetermined gas composition and are of dimensions and configuration effective to cause the rapid equilibration of the dissolved gas composition of a portion of a first fluid in proximity of the elements to reflect the predetermined gas composition of the elements; (b) charging the conduit with a first fluid such that a portion of the fluid is in contact with the gas equilibration reservoir and the gas sensor; (c) recording the response of the gas sensor to the first fluid; (d) displacing the first fluid with a second fluid such that a portion of the second fluid is in contact with the gas sensor and recording the response of the gas sensor to the second fluid; and (e) relating the responses to the gas composition of the second fluid.

Also an objective of the present invention is a method of rapidly equilibrating the dissolved gas composition of a portion of a fluid comprising: (a) providing a conduit having a gas equilibration reservoir containing a predetermined gas composition and of dimensions and configuration effective to cause the rapid equilibration of the dissolved gas composition of a portion of a fluid in contact with the reservoir to reflect the predetermined gas composition contained in the reservoir; and (b) charging the conduit with a fluid such that a portion of the fluid is in contact with the reservoir.

These and other objects of the present invention will be apparent to one of ordinary skill in the art on consideration of the above-presented descriptions and the more detailed descriptions that following immediately, below.

4. BRIEF DESCRIPTION OF THE DRAWINGS

FIGS. 1A, 1B, and 1C illustrate embodiments in which the gas equilibration reservoir comprises a series of head space elements arranged in various ways about the gas sensing means.

5. DETAILED DESCRIPTION OF THE PREFERRED EMBODIMENTS

5.1. The Novel Calibration Method

Figure 1A:
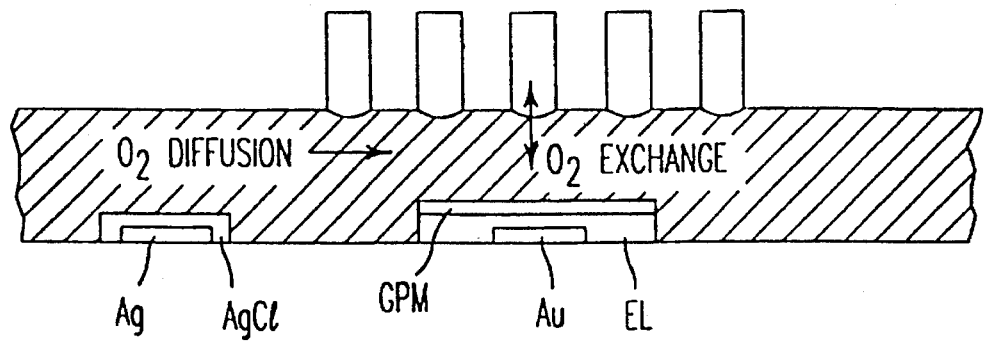
FIG. 1D shows one embodiment in which the gas reservoir comprises a solid/semisolid material placed over the gas sensing means.
FIG. 1E illustrates the use of a gas permeable membrane separating the gas reservoir from the fluid/conduit space.

Clearly, there is an advantage in providing physicians with blood analysis systems that are compact, portable and easy to use at the bedside. This technology is described in U.S. Pat. No. 5,096,669, the entire disclosure of which is incorporated herein by reference. It will be apparent from a consideration of the specification of this patent, however, that providing single-use cartridges with the means for a conventional two-point calibration of the oxygen and carbon dioxide sensors contained therein using the above-described method for bench-top analyzers presents significant engineering problems.

It has been discovered by the present inventors that by microfabricating oxygen sensors and using them in a controlled time domain, i.e., after rapid wet-up for a specified time from the dry state, that it is possible to obtain a consistent background current from device-to-device. This technique, which has been found surprisingly effective, eliminates the need for a "zero" calibration. This technique is also in direct contrast to the methods conventionally used for the calibration of non-microfabricated devices, in which a lack of "dimensional" control over the functional elements makes it necessary to perform a "zero" calibration. For additional details on methods of utilizing microfabricated sensors during wet-up, the reader is referred to the disclosure of U.S. Pat. No. 5,112,455, the complete disclosure of which is incorporated by reference herein.

In addition, it has now been discovered that a microfabricated potentiometric carbon dioxide sensor according to the present invention can also be operated in a controlled time domain, i.e., after rapid wet-up for a fixed time from the dry state, to exhibit a consistent output from device-to-device. This process likewise permits single point calibration. Thus, in one embodiment of the present invention, a single point calibration step is effected by rapidly equilibrating the dissolved gas composition in a calibrant fluid to an oxygen partial pressure of 150 mm Hg and a carbon dioxide partial pressure of 30 mm Hg at 37° C. and contacting the sensor to be calibrated to the equilibrated calibrant fluid.

Equilibration of the calibrant fluid, which comprises an aqueous mixture containing a predetermined concentration of a variety of analyte species (see, for example, the calibrant fluid disclosed in U.S. Pat. No. 5,112,455, the disclosure of which is incorporated in its entirety by reference herein), is achieved by exposing the calibrant fluid to a reservoir of gases of a predetermined composition. It should be noted that while the aqueous calibrant fluid can be rapidly equilibrated by the apparatus and method of the present invention, the sample fluid (typically a sample of whole blood) will generally have a much greater oxygen buffering capacity such that its oxygen concentration will be unaffected by contact with the gas reservoir, which is described in greater detail below.

This oxygen buffering capacity is generally true for blood samples with a partial pressure of oxygen below about 100 mm Hg. However, some blood samples in which the $pO_2$ is well in excess of 100 mm Hg (i.e., the blood contains oxygen well in excess of the buffering capacity of blood), for example, those taken from patients on oxygen therapy, will equilibrate in a manner similar to calibrant fluid. Even under these circumstances it is still possible to obtain an accurate measurement of that dissolved oxygen because the rapid response time of microfabricated sensors allows a measurement to be performed within about ten seconds after the sensors first contact a blood sample. The reduced time for equilibration allows a measurement to be made well before the excess oxygen becomes equilibrated with the reservoir.

In the preferred embodiment, it may be necessary to correct the measurement for variation in the ambient pressure since the invention must operate over the range of barometric pressure usually encountered. For example, if the apparatus is packaged in air at an ambient pressure of 760 mm Hg, but opened at a pressure of 750 mm Hg, e.g. at higher elevation, the air in the reservoir will quickly readjust to 750 mm Hg without changing the relative percentages of gases. Under these circumstances the reservoir will equilibrate with the calibrant fluid to yield a dissolved gas concentration that reflects the partial pressure of that gas in the reservoir. For oxygen, this will be about 20% of 750 mm Hg rather than 20% of 760 mm Hg. By measuring the ambient pressure using the reading device, a correction can be made to the recorded sensor output to account for variation in ambient pressure.

In the present invention, the calibrant fluid is exposed to the gas equilibration reservoir after introduction of the calibrant fluid to a conduit. (The gas sensing means is present in the conduit. In a preferred embodiment of the present invention, this gas sensing means comprises a microelectrode assembly for performing amperometric or potentiometric measurements.) In a preferred embodiment, the calibrant fluid is introduced to the conduit from a storage pack or pouch in which the calibrant fluid can be stored for extended periods. It is important to emphasize that the equilibration/calibration step is performed at the time that the analytical gas composition measurement, itself, is being carried out. Hence, no effort need be expended to control the dissolved gas composition of the calibrant fluid while it is being prepared for storage or during the period of storage within its pouch.

By the apparatus and method of the present invention, the dissolved gas composition of the aqueous calibrant fluid is controlled within a surprisingly short time frame (typically, within 20 seconds to 3 minutes, most typically within 60 seconds) at the point of analysis.

The gas reservoir can take many forms so long as it can be made to hold a predetermined composition of calibrant gases and is able to accommodate the rapid exchange of gases between it and an aqueous calibrant fluid, which is brought into contact with the reservoir, such that the equilibrated gas composition of the aqueous calibrant fluid reflects substantially the predetermined composition of calibrant gases of the reservoir. Essentially, the gas equilibration reservoir comprises a compartment or series of compartments which contain a predetermined composition of gases. The compartment may simply contain the sum of the partial pressures of a variety of calibrant gases. Sometimes, the compartment contains a solid or semisolid material saturated in the predetermined composition of gases.

Figure 1B:
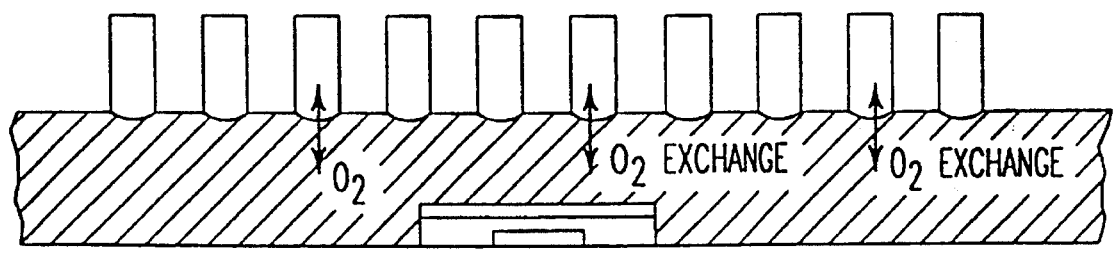
Figure 1C:
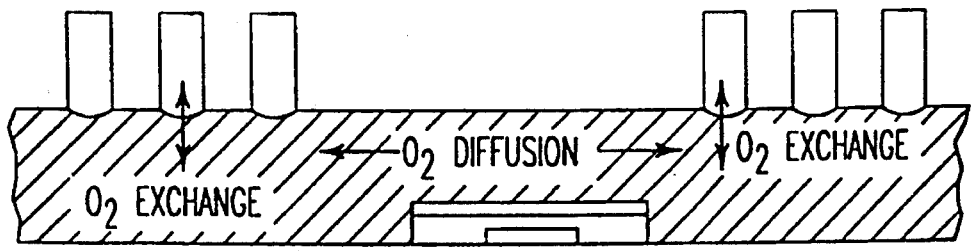

For example, the reservoir, in specific embodiments of the present invention, can be a plurality of head space elements containing the predetermined composition of gases, located in the vicinity of the gas sensing means (see, e.g., FIGS. 1A–1C). In another embodiment, the reservoir can be a solid or semisolid material in which the gases of interest (e.g., carbon dioxide, oxygen, nitrogen, and the like) have a high solubility (see, e.g., FIG. 1D). Suitable solid/semisolid materials include, but are not limited to, silicone rubber, a porous frit, hydrogels, and the like. By hydrogel is meant a hydrophilic gel comprising water and a hydrophilic polymer, including but not limited to, polyethylene oxide, polyvinyl alcohol, polyvinyl pyrrolidone, and the like. As stated above, however, the material must be able to accommodate a high flux of gas through the material.

Figure 1D:
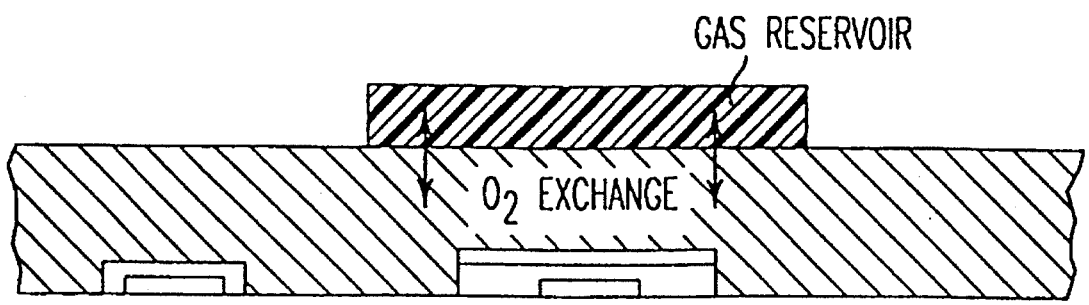
Figure 1E:
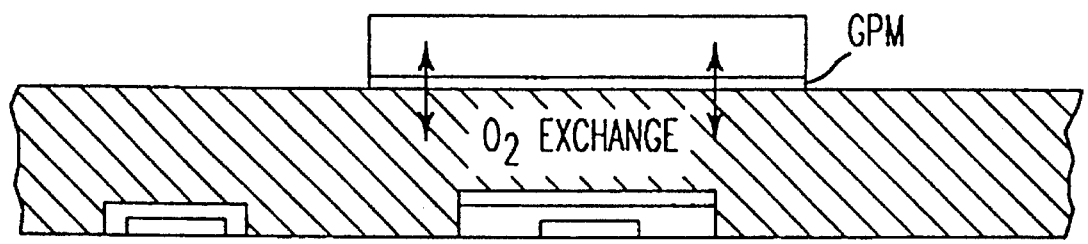

Moreover, the gas reservoir (whether a compartment comprising a head space element(s) or a solid/semisolid material) may be in direct contact with the calibrant fluid or may be separated therefrom by a gas permeable membrane (see, e.g., FIG. 1E). The presence of a gas permeable membrane may offer certain advantages, such as allowing greater control over the dimensions of the calibrant or sample fluids in contact with the gas reservoir or the gas sensing means. Also, the gas permeable membrane may prevent calibrant fluid from inappropriately entering the gas reservoir, especially if the gas reservoir is in the form of a head space element, thus undesirably flushing out the predetermined composition of gases from the gas reservoir.

Furthermore, the volume of the gas reservoir (e.g., the combined volume of a plurality of head space elements, $V_{HS}$) is preferably such that the ratio of gas reservoir volume ($V_{GR}$) to the volume of at least that portion of the calibrant fluid with which the gas reservoir is in direct contact (e.g., the volume of calibrant fluid immediately below the gas reservoir, $V_{CF}$) ranges from about 0.5 to about 5. More preferably, the ratio is approximately 1, most preferably, the ratio is greater than 1. In a specific embodiment, a cartridge is provided having a gas reservoir volume (e.g., $V_{HS}$) which ranges from about 0.5 to 5 µL, preferably about 1 to 3 µL.

Note also that the calibrant fluid may be exposed to a specific region of the conduit rather than to a separate element or reservoir formed in association with the conduit. For example, in FIG. 2B, where the calibrant fluid is positioned to just cover the sensor, the calibrant fluid can equilibrate with the air segment in the part of the conduit directly adjacent to the sensor and, in this case, lying below the head space elements. This situation is, thus, a variant of the method shown in FIG. 2A where the calibrant fluid is first advanced to a reservoir region and then retracted to the position shown in FIG. 2B. Hence, the calibrant fluid may be equilibrated by simply positioning the gas-liquid interface within the conduit close to the sensor, such that the calibrant fluid only just covers the sensor. As with the head space elements or reservoir, the calibrant fluid, with the interface so positioned, will rapidly equilibrate with the predetermined composition of gases present in the adjacent part of the conduit.

Figure 2A:
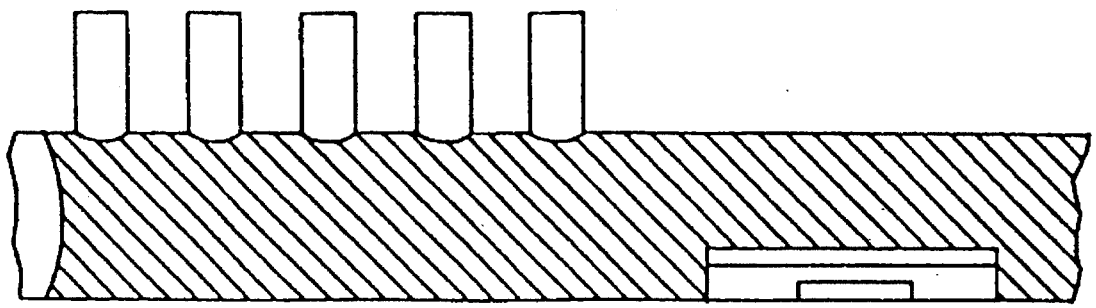
FIGS. 2A and 2B illustrate a sequence in which the calibrant fluid is equilibrated in a region lying beyond the sensor region, then retracted back over the sensor region for the calibrating step. The calibrant fluid would then be displaced by sample fluid.
Figure 2B:
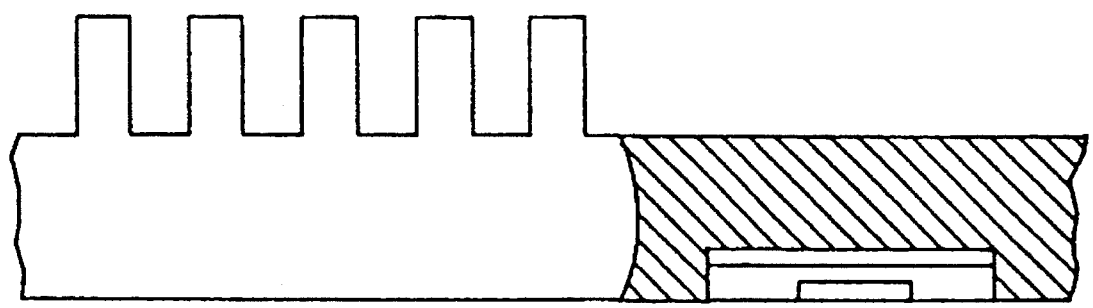
Figure 4:
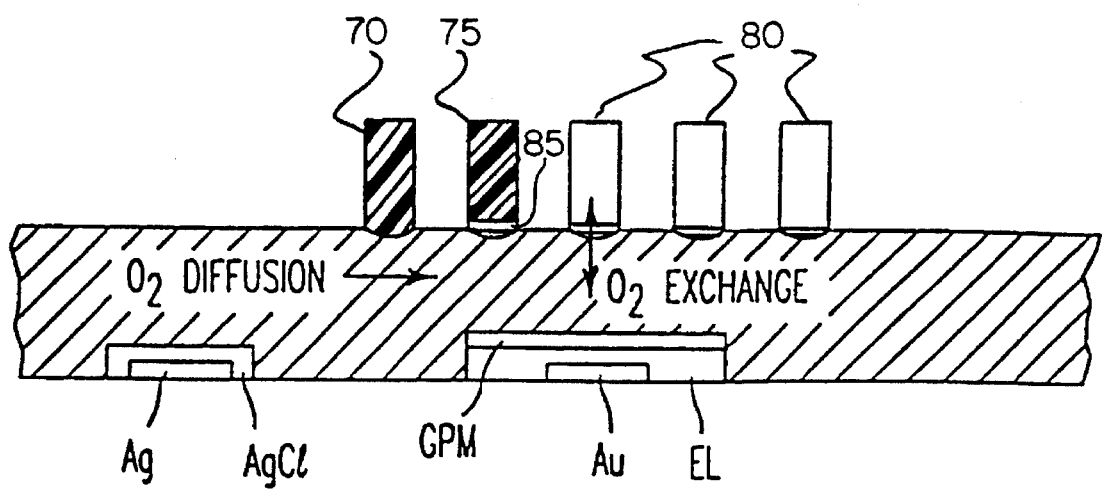
FIG. 4 illustrates a gas equilibration reservoir comprising a solid or semisolid material (70), a gas permeable membrane separating a reservoir comprising a solid or semisolid material (75) from the conduit and a gas permeable membrane separating a reservoir comprising head space elements (80) from the conduit.
Figure 3:
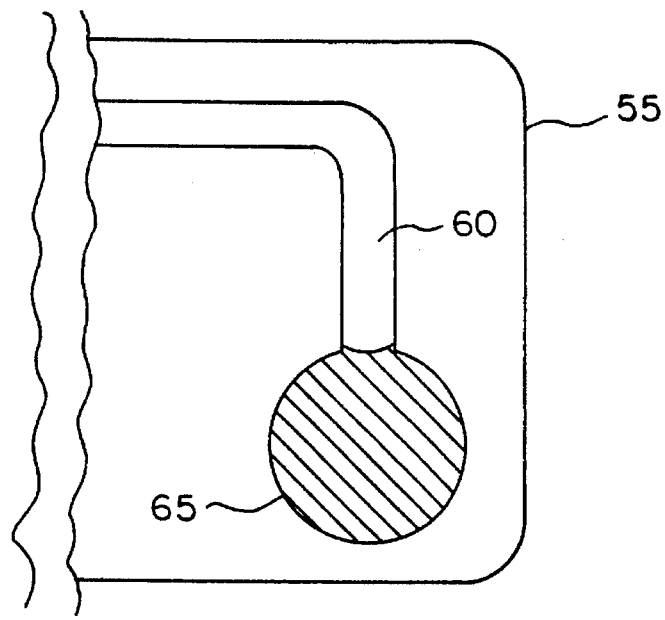
FIG. 3 illustrates a conduit (60) within a housing (55), which conduit is joined to a calibrant fluid region (65).

The position of the gas-liquid interface can be controlled optically (either visually or with an optical sensor) or by the response of the gas sensing means, itself. Preferably, the conduit is equipped with a conductivity sensor for determining the position of the interface. As shown in FIG. 2B, the interface is preferably positioned just past the gas sensing means. Suitable conductivity sensors may be produced as described, for example, in U.S. Pat. No. 5,200,051, who complete disclosure is incorporated by reference herein.

Accordingly, the present invention also contemplates a method of rapidly equilibrating the dissolved gas composition of an aqueous fluid, which is used to calibrate a gas sensing means within a conduit, comprising: (a) charging a conduit with an aqueous fluid, the conduit containing a predetermined composition of gases and equipped with a gas sensing means for measuring the concentration of dissolved gas in a fluid sample; (b) positioning the gas-liquid interface of the aqueous fluid just past the gas sensing means, such that the distance between the interface and that portion of the aqueous fluid, which is in contact with the gas sensing means, is substantially minimized.

In a preferred embodiment of the invention, the gas sensing means, conduit, and calibration fluid pack are contained in a disposable housing, which, in turn, is stored in a sealed package. Thus, the present invention takes advantage of the relative ease by which the atmosphere within the sealed package can be controlled in the packaging process. For instance, the package atmosphere can be set to contain 20% oxygen and 80% nitrogen. Consequently, the predetermined composition of gases in the gas reservoir will be the same, i.e., 20% oxygen and 80% nitrogen. At the time of performing the fluid dissolved gas analysis, the package containing the preferred disposable housing is opened, dissipating the pre-packaging controlled atmosphere. However, because of the circuitous nature of the housing assembly and the conduits contained therein, the predetermined composition of gases present in the gas reservoir (which correspond to the pre-packaging controlled atmosphere) has been found to remain substantially unchanged over a sufficient period of time (about three to five minutes), such that the operator can introduce the sample fluid to the disposable housing assembly, release and equilibrate the calibrant fluid to reflect the desired dissolved gas composition. It has been found that the time required for removing the disposable unit from the package, charging it with fluid sample, and equilibrating the calibrant fluid over the gas sensing means ranges from one to five minutes. Preferably, one goes through the operation of removing the disposable unit from the package to bringing calibrant fluid in contact with gas reservoir within about two minutes. The gas reservoir of the present invention retains the predetermined composition of gases over at least three minutes after the package is opened. If the predetermined composition is essentially the composition of air, then the predetermined composition is of course stable indefinitely.

5.2. Temperature Effects

The solubility of all gases in liquids decreases with increasing temperature. Any device that measures the partial pressure of oxygen or carbon dioxide in blood requires thermostating at 37° C. Thermostating is especially important for oxygen measurements, in which binding to hemoglobin exhibits a significant temperature dependence. Obviously, the calibrant fluid must also be at 37° C. In a preferred embodiment of the present invention, the calibrant fluid, which may have been stored below room temperature, is rapidly heated to a temperature of 37° C. where it is maintained for the calibration/equilibration step and subsequent dissolved gas measurement step.

In the preferred disposable cartridge, thermostated heating of the sensors, calibrant and sample is achieved with a resistive heater on the sensor chip. One should note that one embodiment of the instrument that operates the single-use cartridge may be powered by a battery. Thus, there may be a premium associated with heating, and it should be provided only where and when it is essential. However, only the region of the cartridge where calibration and sample measurement are performed requires heating.

In devising a means for performing a blood gas measurement with only the single point calibration, it is important to understand the thermal history of both the calibrant and blood sample prior to the measurement. The nature of and the changes in these parameters necessarily determine the design requirements for the cartridge.

Typically, the calibrant starts at room temperature, since it is contained within the cartridge which is stored at that temperature. Consequently, when the calibrant pack is pierced and the calibrant fluid moves to contact the heated sensor chip, the calibrant fluid will tend to lose dissolved gases. In fact, the assembly of the cartridge results in the calibrant pack being compressed at about 1.1 atmospheres so that the fluid also tends to de-gas when the calibrant pack is pierced because of the consequent reduction in the total pressure.

An arterial blood sample will be withdrawn from the patient at 37° C. and then be introduced to the cartridge where it will cool to room temperature. As it cools the affinity of hemoglobin for oxygen increases and the partial pressure of oxygen will decrease. When the blood is moved to the sensor region it must be re-heated to 37° C. to establish the original partial pressure of oxygen.

5.3. Cartridge Design And Head Space Elements

Given the above-described considerations, it has now been discovered that a cartridge design that incorporates a series of head space elements accessible to the calibrant fluid can rapidly equilibrate the dissolved gas composition of the calibrant fluid to a predetermined level at ambient pressure and at a temperature ranging from about ambient to about physiological temperature, e.g., 37° C. For example, it has been found that a calibrant fluid can be quickly brought to a state of equilibrium with ambient air, to provide a dissolved oxygen content of 20%, simply by bringing the calibrant fluid in the proximity of the head space elements incorporated into the cartridge design of the present invention.

Moreover, it has been observed that the instant head space elements reliably maintain the original partial pressure of oxygen in the fluid sample after the fluid sample has displaced the equilibrated calibrant fluid from the sensing means. As mentioned above, a number of fluid samples can be analyzed according to the present invention, including biological fluids such as blood, plasma or urine. It must be stressed that the present invention does not merely involve the calibration of an instrument in ambient air. Rather, the present invention, in one embodiment, allows ambient air to control the dissolved gas composition in a calibrant fluid, which is in turn used to perform a single-point calibration of the sensor.

The use of ambient air is most convenient. However, as one of ordinary skill in the art will appreciate from the crux of the instant disclosure, any mixture of gases can be introduced into the head space elements of the present invention to control the resultant dissolved gas composition of a fluid which is subsequently brought into proximity or contact with the head space elements.

Turning now to the figures, FIGS. 1A, 1B, and 1C show cartridge designs that allow the inclusion of one or more head space elements within the fluid conduit, in the vicinity of the sensing means. These head space elements may be filled with ambient air, preferably at ambient pressure, which elements when first coming into contact with an aqueous calibrant fluid provide a sufficient oxygen source (or sink) to allow the rapid equilibration of that fluid to reflect the ambient partial pressure of the particular mix of gases in the head space elements. However, when the aqueous calibrant fluid is displaced from the head space region, e.g., by a blood sample, there is insufficient oxygen in the head space elements to change the partial pressure of oxygen in the blood sample on the time scale of the measurement. Moreover, the partial pressure of oxygen in blood is less likely to change owing to the much greater oxygen buffering capacity of whole blood. It may thus be said that the present method uses to the operator's advantage the recognition of the differences in the oxygen buffering capacities of blood relative to aqueous fluids and the consequences of contacting air contained in a plurality of head space elements with these two types of fluid for short, controlled periods of time. While this premise is generally true, blood samples taken from patients undergoing oxygen therapy may have oxygen levels in their blood which exceed the buffering capacity of hemoglobin. In those circumstances in which the blood may behave like a calibrant fluid, it may be necessary to take into account the equilibration of the blood sample with the reservoir (e.g., if it is desirable to delay measurement of the fluid sample beyond the first ten seconds after calibrant-to-fluid sample transition) by extrapolating the output signal back to the calibrant-to-fluid sample transition, as described in U.S. Pat. No. 5,112,455 or utilizing a reservoir embodiment in which the reservoir is not directly above the sensor as shown in FIGS. 1C, 2A, and 2B herein.

Once more, it is noted that the head space element is made to contain a sufficient amount of a preselected gas composition such that exposure to the head space element dictates the dissolved gas composition of a standard aqueous fluid. If one calibrates with ambient air, i.e., 20% oxygen, the concentration of oxygen in the head space element will be 0.2/22.4=8.9 millimoles per liter of gas. At 37° C. an ambient air equilibrated aqueous solution will be about 0.26 mM oxygen. Consequently, if the aqueous fluid is within about 25% of this value beforehand, the head space element will have more than sufficient oxygen to cause the rapid equilibration of the fluid to within 1.0% of the desired value. This assumes the distance between the head space element and the sensor is small, e.g., less than 1 mm, and the volume of the head space element is roughly the same as the volume of fluid it is equilibrating.

It should further be noted that when the calibrant pack is pierced and the fluid ejected over the sensors, some fraction of the air in the pack moves ahead of the fluid and can potentially wash-out the contents of the head space elements. However, it has been found that by adjusting the volume of the head space element, it is possible to control whether: (i) the fluid re-equilibrates with the air that was in the calibrant pack, but which is now adjusted to ambient pressure, or (ii) the fluid equilibrates with the air originally in the head space element.

For bedside measurements, it is important that the results are obtained quickly. Consequently, the embodiments shown in FIGS. 1A–1E enable rapid equilibration. It has been found that the rate is much faster than that expected from diffusion alone. This is because heating induces a convective mixing of the fluids.

The specific embodiments shown in the figures have the following attributes. FIG. 1A positions the head space element directly over the sensor. However, while equilibration is taking place, oxygen in the adjacent fluid is transported to the sensor region by diffusion and convection. The design shown in FIG. 1B ensures full equilibration around the sensor. FIG. 1C is another embodiment that should prove useful when the calibrant fluid must lose oxygen. In addition, FIG. 1C ensures that the blood sample is not in contact with the head space elements, which may have now been enriched in oxygen, when the blood sample is positioned directly over the sensor. FIG. 1D illustrates a gas equilibration reservoir comprising a compartment containing a solid/semisolid material in which the calibrant gases have a high solubility and through which the gases have a high rate of diffusion. A gas permeable membrane separating the gas reservoir compartment from the conduit is shown in FIG. 1E.

FIGS. 2A and 2B show yet another embodiment of the present method. Here the calibrant fluid is first moved past the sensor to contact the head space element and allowed to equilibrate. Then the calibrant fluid is retracted to the sensor. Positioning of the fluid can be achieved by means of a conductivity sensor that detects the fluid's position relative to one of the sensors. The fluid can also be oscillated in the head space region to accelerate the equilibration process.

The foregoing serves to illustrate the present invention and should not be construed as limiting the invention in any way. Other embodiments are readily apparent to those of ordinary skill in the art after consideration of the descriptions and preferred embodiments presented herein. These embodiments are considered to fall within the scope and spirit of the present invention, which is limited solely by the following claims.

What is claimed is:

1. An apparatus for the rapid equilibration of the dissolved gas composition of an aqueous calibrant fluid comprising:
    (a) a housing, including a calibrant fluid region which holds an aqueous calibrant fluid apart from a gas equilibration reservoir wherein said aqueous calibrant fluid has dissolved gases;
    (b) at least one conduit within said housing joined to said calibrant fluid region, which conduit can be charged with said aqueous calibrant fluid held in said calibrant fluid region; and
    (c) said gas equilibration reservoir positioned in said conduit wherein said reservoir contains a predetermined composition of calibrant gases such that when said aqueous calibrant fluid is charged into said conduit and brought in contact with said reservoir said calibrant fluid undergoes an exchange of said aqueous calibrant fluid's dissolved gases with calibrant gases contained in said reservoir to provide an aqueous calibrant fluid with an equilibrated dissolved gas composition that reflects substantially the predetermined composition of calibrant gases contained in said reservoir.

2. The apparatus of claim 1 in which said reservoir includes a compartment filled with a solid or semisolid material that functions as a source of a predetermined composition of calibrant gases.

3. The apparatus of claim 1 in which said reservoir includes a compartment filled with a solid or semisolid material that functions as a sink with a predetermined composition of calibrant gases.

4. The apparatus of claim 2 in which said material comprises silicone rubber.

5. The apparatus of claim 3 in which said material comprises silicone rubber.

6. The apparatus of claim 2 in which said material comprises a hydrogel.

7. The apparatus of claim 3 in which said material comprises a hydrogel.

8. The apparatus of claim 1 in which said reservoir includes a head space element.

9. The apparatus of claim 1 in which said reservoir includes a plurality of head space elements.

10. The apparatus of claim 8 in which said head space element functions as a source of or a sink with a predetermined composition of calibrant gases.

11. The apparatus of claim 9 in which said head space element functions as a source of or a sink with a predetermined composition of calibrant gases.

12. The apparatus of claim 2 which further comprises a gas permeable membrane that separates said reservoir from said conduit.

13. The apparatus of claim 3 which further comprises a gas permeable membrane that separates said reservoir from said conduit.

14. The apparatus of claim 8 which further comprises a gas permeable membrane that separates said reservoir from said conduit.

15. The apparatus of claim 9 which further comprises a gas permeable membrane that separates said reservoir from said conduit.

* * * * *